US009251809B2

(12) United States Patent
Reiner

(10) Patent No.: US 9,251,809 B2
(45) Date of Patent: Feb. 2, 2016

(54) METHOD AND APPARATUS OF SPEECH ANALYSIS FOR REAL-TIME MEASUREMENT OF STRESS, FATIGUE, AND UNCERTAINTY

(71) Applicant: Bruce Reiner, Berlin, MD (US)

(72) Inventor: Bruce Reiner, Berlin, MD (US)

(*) Notice: Subject to any disclaimer, the term of this patent is extended or adjusted under 35 U.S.C. 154(b) by 258 days.

(21) Appl. No.: 13/898,916

(22) Filed: May 21, 2013

(65) Prior Publication Data
US 2013/0311190 A1 Nov. 21, 2013

Related U.S. Application Data

(60) Provisional application No. 61/649,723, filed on May 21, 2012.

(51) Int. Cl.
| | |
|---|---|
| *G10L 21/00* | (2013.01) |
| *G10L 13/00* | (2006.01) |
| *G10L 25/48* | (2013.01) |
| *G06Q 50/22* | (2012.01) |
| *G06Q 10/06* | (2012.01) |
| *G06Q 30/02* | (2012.01) |
| *G06F 19/00* | (2011.01) |

(52) U.S. Cl.
CPC ............ *G10L 25/48* (2013.01); *G06Q 10/0633* (2013.01); *G06Q 10/0639* (2013.01); *G06Q 30/0201* (2013.01); *G06Q 50/22* (2013.01); *G06F 19/34* (2013.01)

(58) Field of Classification Search
None
See application file for complete search history.

(56) References Cited

U.S. PATENT DOCUMENTS

| | | | | |
|---|---|---|---|---|
| 5,897,616 | A * | 4/1999 | Kanevsky et al. | 704/246 |
| 7,809,572 | B2 * | 10/2010 | Yamagami | G10L 13/10 704/200 |
| 8,805,756 | B2 * | 8/2014 | Boss et al. | 706/12 |
| 8,812,319 | B2 * | 8/2014 | Skerpac | 704/246 |
| 2013/0132308 | A1 * | 5/2013 | Boss et al. | 706/12 |
| 2013/0159413 | A1 * | 6/2013 | Davis et al. | 709/204 |
| 2013/0197968 | A1 * | 8/2013 | Davis et al. | 705/7.29 |

* cited by examiner

*Primary Examiner* — Satwant Singh
(74) *Attorney, Agent, or Firm* — Jean C. Edwards, Esq.; Edwards Neils PLLC

(57) ABSTRACT

The present invention utilizes speech analysis to provide real-time measurement of end-user stress, fatigue, and uncertainty in decision-making. The present invention monitors "technology-induced" stressors by increasing the inherent functionality of individual monitoring technologies, so as to perform multiple applications in a single setting. In addition to the continued use of speech recognition technology for computerized report transcription, the present invention simultaneously measures and analyzes occupational stress and fatigue in real-time, specific to the unique profile of each individual end-user and context of the task being performed. The derived user-specific stress/fatigue analytics may be used in the creation of a number of workflow and quality enhancing deliverables, including customizable intervention strategies for stress/fatigue reduction, creation of automated workflow templates, and targeted quality assurance and peer review.

38 Claims, 6 Drawing Sheets

METHOD AND APPARATUS OF SPEECH ANALYSIS FOR REAL-TIME MEASUREMENT OF STRESS, FATIGUE, AND UNCERTAINTY

CROSS-REFERENCE TO RELATED APPLICATIONS

The present application claims priority from U.S. Provisional Patent Application No. 61/649,723, filed May 21, 2012, the contents of which are herein incorporated by reference in their entirety.

BACKGROUND OF THE INVENTION

1. Field of the Invention

The present invention relates to speech analysis to provide real-time measurement of end-user stress, fatigue, and uncertainty in decision-making.

2. Description of the Related Art

Speech recognition technology is currently in widespread use for computerized report transcription in a number of professional fields including medicine. As medicine has undergone a wholesale transition from analog (i.e., paper-based) to digital (i.e., computerized) practice, speech recognition technology has been one of the fundamental drivers in the process. A number of operational, economical, and efficiency benefits are derived through its use including the digitization of medical data, elimination of third party transcription services, ability to archive data into a centralized database, and markedly improved report turnaround and communication. Medical reports which previously required days for delivery can now be finalized and communicated in minutes, which improves the timeliness of healthcare delivery and in theory, can lead to improved clinical outcomes. Along with these derived benefits in operational efficiency and data management, adoption of speech recognition technology does come at a cost. By transferring editing and transcription responsibilities to the end-user (i.e., radiologist), use of speech recognition can result in decreased productivity, which is of particular importance in the current medical practice environment of reduced economic reimbursements, increased data volume and complexity, and heightened expectations in service delivery. These combined pressures have exacerbated the increased occupational stress and fatigue experienced by healthcare professionals, which has been shown to be associated with increased errors, which is in turn can lead to adverse events and diminished healthcare outcomes.

A number of landmark publications have been issued from the Institute of Medicine which have highlighted the unexpectedly high frequency of medical errors and occupational stress/fatigue among healthcare professionals. Technology has been a double-edged sword for healthcare providers: on the one hand, it has dramatically improved the quality and accessibility of data, while on the other hand, it has created heightened expectations on the part of consumers and increased stress on the part of service providers, which is highly variable in accordance with the individual end-user's technology proclivity, education/training, and occupational demands.

Thus, a way of addressing these "technology-induced" stressors and to monitor in real-time, the end-user's stress, fatigue, and uncertainty in speech patterns, is needed.

SUMMARY OF THE INVENTION

The present invention utilizes speech analysis to provide real-time measurement of end-user stress, fatigue, and uncertainty in decision-making. The present invention relates to monitoring "technology-induced" stressors by increasing the inherent functionality of individual monitoring technologies, so as to perform multiple applications in a single setting. In addition to the continued use of speech recognition technology for computerized report transcription, the present invention simultaneously measures and analyzes occupational stress and fatigue in real-time, specific to the unique profile of each individual end-user and context of the task being performed. The derived user-specific stress/fatigue analytics may be used in the creation of a number of workflow and quality enhancing deliverables, including customizable intervention strategies for stress/fatigue reduction, creation of automated workflow templates, and targeted quality assurance and peer review.

Numerous studies have shown that healthcare providers experience variable levels of uncertainty in decision-making, which can negatively impact the quality, economics, and timeliness of healthcare delivery. Uncertainty in healthcare decision-making can potentially result in delayed diagnosis and treatment, increased cost (by ordering additional tests and consultations), misunderstanding (through the introduction of ambiguous and vague information), and error. The creation of a computerized tool which could measure uncertainty in real-time (i.e., at the point of care) could in theory provide valuable insight and education to the end-user, while also serving as a trigger for computerized decision-support technologies and expert (third party) consultations. The present invention expands the functionality of speech analysis by reducing occupational stress/fatigue, while simultaneously improving the economics and quality of healthcare deliverables.

The present invention makes reference to U.S. patent application Ser. No. 13/537,976, filed Jun. 29, 2012—the contents of which are herein incorporated by reference in their entirety—which includes a number of stress/fatigue measurement tools which may be integrated with the present invention, for measuring visual, physiologic, and cognitive forms of stress/fatigue. However, the present invention requires the integration of a new stress/fatigue measurement device based upon established methods of speech analysis. These novel speech-derived stress/fatigue analytics can be used in isolation or combination with other described stress/fatigue measures.

One novel feature of the present invention is that it is directly integrated into longitudinal workflow analysis, thereby creating an extended view (and analysis) of the individual end-user's occupational stress/fatigue, as opposed to a single "snapshot" or short-term analysis of speech derived stress/fatigue. In addition, the present invention takes into account a number of unique variables into the analyses including (but not limited to) the individual end-user profile, task being performed, technology in use, workflow, and outcomes measures. The end result is that the present invention not only provides a real-time measure of occupational stress/fatigue, but also provides insights as to how these dynamic stress/fatigue measures correlate with use patterns, technology, individual end-user characteristics, and performance outcomes. This latter feature (i.e., correlation between occupational stress/fatigue and performance outcomes) is an important attribute of the invention which sheds important light as to defining "best practices" guidelines and standards.

Another important and novel feature of the present invention is the use of speech analysis to measure uncertainty in task performance. In professions where rapid and intense decision-making is required (e.g., medicine, aviation, military); analysis of speech for uncertainty can be extremely valuable in detecting instances in which successful task performance may be compromised due to cognitive limitations on the part of the end-user, which may in part be related to high stress/fatigue levels. By identifying higher than normal levels of uncertainty in real-time, the present invention provides valuable insight to the end-user, as well as prompting the use of alternative decision-making resources (i.e., computerized decision support, consultations of third parties). In addition, the present invention provides a mechanism for correlating user-specific uncertainty measures with task complexity, technology in use, and performance outcome measures. By demonstrating through longitudinal data analysis the specific circumstances in which uncertainty is associated with poor outcomes, this provides a valuable data-driven tool for optimizing resource allocation and workflow distribution in order to maximize the quality and accuracy of desired outcomes.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention utilizes speech analysis to provide real-time measurement of end-user stress, fatigue, and uncertainty in decision-making. The present invention relates to monitoring "technology-induced" stressors by increasing the inherent functionality of individual monitoring technologies, so as to perform multiple applications in a single setting. In addition to the continued use of speech recognition technology for computerized report transcription, the present invention simultaneously measures and analyzes occupational stress and fatigue in real-time, specific to the unique profile of each individual end-user and context of the task being performed. The derived user-specific stress/fatigue analytics may be used in the creation of a number of workflow and quality enhancing deliverables, including customizable intervention strategies for stress/fatigue reduction, creation of automated workflow templates, and targeted quality assurance and peer review.

Figure 1:
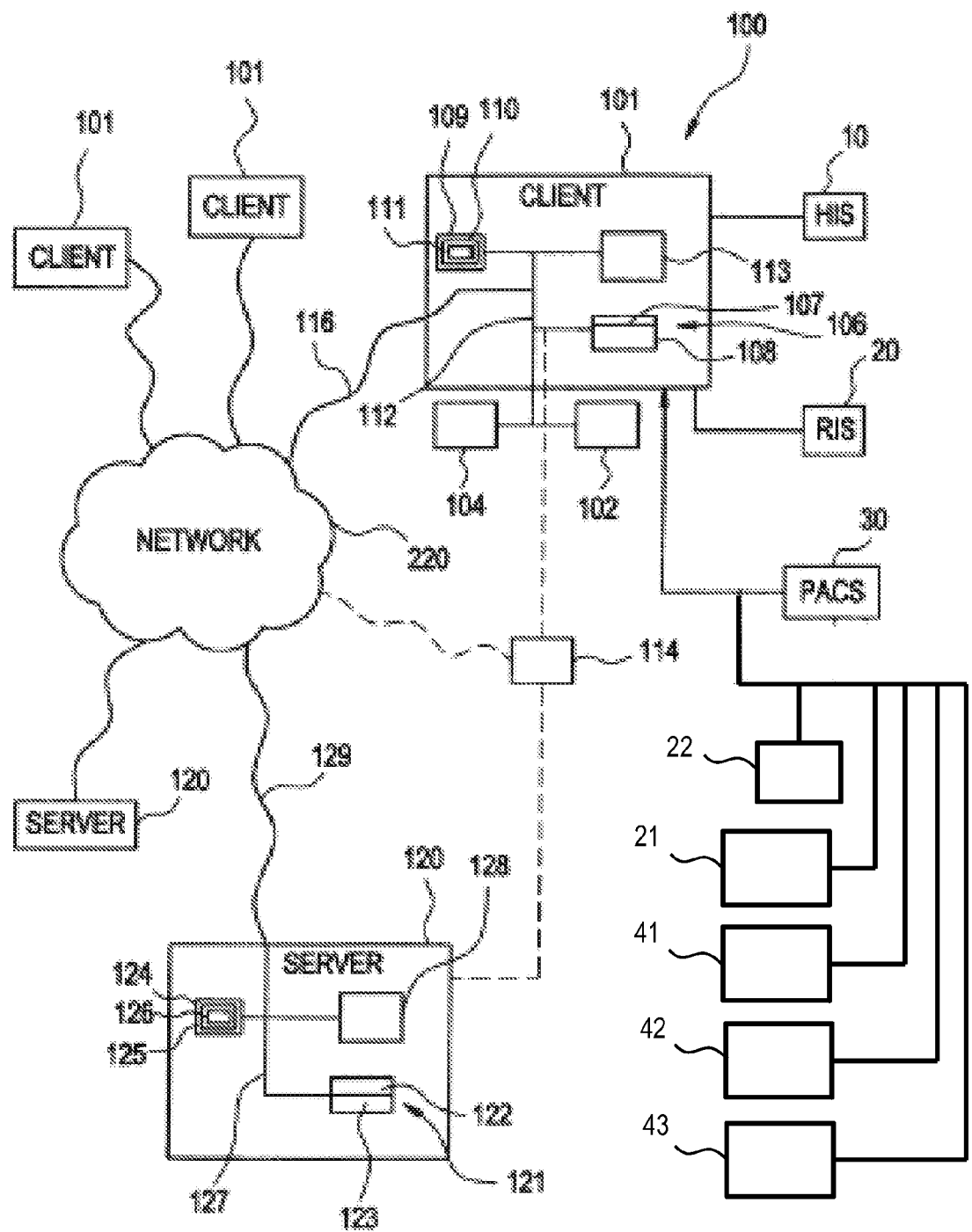
FIG. 1 is a schematic diagram of a system for monitoring speech patterns in real-time, according to one embodiment consistent with the present invention.

According to one embodiment of the invention illustrated in FIG. 1, medical applications may be implemented using the system 100. The system 100 is designed to interface with existing information systems such as a Hospital Information System (HIS) 10, a Radiology Information System (RIS) 20, an acquisition or radiographic device 21, and/or other information systems that may access a computed radiography (CR) cassette or direct radiography (DR) system, a CR/DR plate reader 22, a Picture Archiving and Communication System (PACS) 30, a biometrics system 41, stress analysis system(s) 42, speech analysis system 43, and/or other systems, which are connected to the patient to record certain metrics. The system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the system 100 of the present invention and the information systems, such as the HIS 10, RIS 20, radiographic device, CR/DR plate reader 22, and PACS 30, etc., may be enabled to allow the system 100 to retrieve and/or provide information from/to these systems. According to one embodiment of the invention, bi-directional communication between the system 100 of the present invention and the information systems allows the system 100 to update information that is stored on the information systems. According to one embodiment of the invention, bi-directional communication between the system 100 of the present invention and the information systems allows the system 100 to generate desired reports and/or other information.

The system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, or other input device 104.

According to one embodiment of the invention, the input or other selection device 104 may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection.

According to another embodiment of the invention, symbols and/or icons may be entered and/or selected using an input device 104, such as a multi-functional programmable stylus. The multi-functional programmable stylus may be used to draw symbols onto the image and may be used to accomplish other tasks that are intrinsic to the image display, navigation, interpretation, and reporting processes. The multi-functional programmable stylus may provide superior functionality compared to traditional computer keyboard or mouse input devices. According to one embodiment of the invention, the multi-functional programmable stylus also may provide superior functionality within the PACS and Electronic Medical Report (EMR).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the image display device 102 may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the system 100 may include separate programs 110 having code that performs desired operations. According to one embodiment of the invention, the program 110 that runs the system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, the system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, and the PACS 30 (if separate) are shown as directly coupled to the client computer 101, it is known that these systems may be indirectly coupled to the client over a LAN, WAN, the Internet, and/or other network via communication links. According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems of the present invention may contain additional or different components.

The present invention makes reference to U.S. patent application Ser. No. 13/537,976, filed Jun. 29, 2012, the contents of which are herein incorporated by reference in their entirety, which includes a number of stress/fatigue measurement tools which may be integrated with the present invention, for measuring visual, physiologic, and cognitive forms of stress/fatigue. Measurements of speech for stress/fatigue and uncertainty are discussed in more detail below. However, generally, there are two fundamental tenets or assumptions in the creation of the speech analysis system 43 of the present invention; namely, speech is unique to each individual and has unique attributes, and the characteristics of each person's speech can be used to create a personalized speech profile. The combination of these two principles can in turn be used to create a technology which can serve three different functions in isolation or combination:

1. End-user identification/authentication;
2. Real-time measurement and characterization of stress; and
3. Real-time measurement of uncertainty in decision-making.

The creation of personalized speech profiles takes advantage of the fact that no two end-user's speech patterns are identical, and speech can therefore serve as an auditory fingerprint of the individual, using a speech analysis device 43, which can be used in lieu of traditional biometrics devices 41 (e.g., fingerprint or retinal scanning) for identification and authentication. The use of speech analysis for end-user identification/authentication has a unique benefit not attributable to traditional biometrics, in that speech analysis is dynamic. This unique ability of the speech analysis system 43 of the present invention provides a mechanism to not only identify and authenticate an individual end-user, but also to determine subtle changes in that individual's affect, emotion, or stress over time. This provides the benefit of dynamically tailoring use and authentication to pre-determined levels of stress or emotion for each individual end-user. To illustrate how this dynamic identification/authentication function of speech analysis would work, three examples showing different aspects of the invention as directed to a physician, security personnel, and pilot, are described below.

In all three occupational settings, security mandates require an individual end-user be correctly identified and authenticated before getting access to sensitive information and/or technology. In the case of the physician, this sensitive information and technology includes secure healthcare data which is contained within various types of information system technologies (e.g., electronic patient record (EPR)). In order to determine a certain physician (or other healthcare professional) has the appropriate authorization to view specific healthcare data, they must first undergo identification and authentication by a computer biometrics system 41. If they are properly credentialed and authorized by the program 110 of the computer system 110 of the present invention, to view the data and use the technology in question, they will be granted access by the computer biometrics system 41 once the identification/authentication process has been successfully completed.

On a secondary level however, authorization of data/technology access is not always a binary function, but in some instances may be conditional in nature, in accordance with some specific attribute of the individual at that particular time of identification/authentication. As an example, the physician in question is a neurosurgeon, and in one instance, he/she may simply want access to personalized healthcare data of one of their patients, which only requires that the physician in question has been granted access by the biometrics system 41 to the hospital's information system (i.e., his/her hospital privileges are active and in good standing), and the patient in question has listed that particular physician as one of his/her designated healthcare providers. For this specific purpose, once identification/authentication of the neurosurgeon's has been successfully completed on the computer system/biometrics system 41, access to the patient's data is granted by the computer program 110 without specific restrictions.

In one example of use, the same thoracic surgeon is scheduled to perform a specific surgical procedure or operation on a patient, which requires use of a specialized technology (e.g., gamma knife). In addition to the computer program 110 requiring end-user identification and authentication by the biometrics system 41 (to determine if the individual end-user in question credentialed and authorized to use the technology in question and perform the designated procedure), a second level of identification/authentication is required by the computer program 110, which dynamically analyzes the emotional state of the individual end-user prior to authorization. This second level of identification/authentication may evaluate the emotional, physical, or cognitive states of the neurosurgeon prior to granting access to the computer system 110 or other technology to perform the requested procedure.

Examples of how speech analysis can be used for this dynamic form of end-user identification/authentication may include (but are not limited to) measures of stress by the speech analysis system 43 in the evaluation of restfulness (e.g., sleep deprivation), sobriety (e.g., alcohol intake), and emotion (e.g., depression or anxiety). The idea is that the identification/authentication process can be dynamically adjusted by the program 110 of the computer system 100 in keeping with context and user-specific parameters.

In the case of context, the procedure in question (e.g., gamma knife brain biopsy) requires that a minimum level of stress be measured prior to performance of the procedure due to the complexity of the task and high risk of complication. In the event that the neurosurgeon in question was found to have an unacceptably high level of analysis of his/her personalized speech profile, the computer program 110 would prohibit access of the neurosurgeon to the technology required, provide him/her with the recorded data, analysis, and measurement requirements, and notify all associated personnel (e.g., department chief, hospital administrator, quality assurance officer, nursing supervisor) within the medical institution, by electronic means (i.e., dialog box, text, email, facsimile, etc.) of the identification/authentication failure. An appeal process would be incorporated into the computer program 110 which would provide the neurosurgeon with the ability to re-attempt the authentication process at a designated time period (e.g., 1 hour delay), utilize an alternative technology for stress measurement (e.g., physiologic stress measurement using galvanic skin response), or formal appeal to an authorized third party (e.g., hospital administrator). In all examples, the derived data would be recorded in identification/authentication databases 113 (i.e., of the hospital, physician, department, and patient) for the purposes of longitudinal analysis, quality assurance, and compliance. Access to the requisite technology would be effectively "locked down" by the computer program 110 until the appropriate clearance was achieved.

In addition to pre-determined stress measures in accordance with the specific context (i.e., neurosurgical procedure to be performed), the stress measure requirements could also be adjusted by the program 110 in accordance with the individual end-user profile. In this example, suppose the neurosurgeon in question has had a prior history of alcohol or drug use which has resulted in past performance problems and a temporary suspension in his/her privileges. In this particular example, the degree of scrutiny and type of analysis by the program 110 may be slightly different for the same context (e.g., gamma knife biopsy) for this neurosurgeon as opposed to one of his/her colleagues without a prior history of alcohol/drug use. While another neurosurgeon may be simply asked by the program 110 to undergo a fairly routine speech analysis for stress, the neurosurgeon with the prior alcohol history may be required by the program 110 to undergo a more rigorous speech analysis (e.g., extended and/or more complex speech samples), along with the possibility of alternative test procedures (e.g., tests of dexterity and/or cognitive skills).

The ability of the program 110 of the present invention to create and constantly update and refine each individual end-user's personalized speech profile creates a unique and powerful tool for identification/authentication. Subtle changes in speech over time provide a mechanism for the program 110 to continuously update the speech profile along with the ability to detect subtle variation in speech from the individual end-user's baseline. The ability of the program 110 to correlate real-time (i.e., contemporaneous) analysis of speech with a data rich and comprehensive personalized speech profile baseline stored in the database 113, provides the program 110 of the present invention, the ability to more accurately and reliably detect subtle changes in stress level than would a static biometrics tool 41 (e.g., fingerprint or retinal scan). The net result is that speech analysis and personalized speech profiles can collectively be used by the program 110 for both static and dynamic end-user identification and authentication, which can be modified by the program 110 in accordance with the context and user-specific requirements.

In another example, dynamic identification and authentication of a security analyst with a governmental agency (e.g., National Security Agency (NSA)), who is tasked with analysis of high-security and classified documents, is examined. In order to gain access to these highly classified documents, this security officer must undergo identification/authentication to access a computer system 100, which traditionally consists of being tested at a static biometrics device 41. Using a speech analysis system 43 of the present invention, and its dynamic capabilities to detect stress, one could envision the unique value of the present invention for identification/authentication, which could be used in isolation or tandem with conventional biometrics technologies 41. In this example, the "allowable" level of stress could be adjusted by the program 110 in accordance with the sensitivity and classification of the data being accessed by the user. A top-security document would not only require the appropriate authorization of a limited number of end-users, but also require extremely low measured levels of stress (using speech analysis) for identification/authentication to be accepted. The ability of the program 110 to track speech analytics using a speech analysis system 43, and record and analyze the speech analytics data in the centralized database 113, provides an additional valuable tool for analysis.

In an alternative example, an individual security analyst was found to have a slightly higher than normal measured stress level in his/her speech during a specific identification/authentication process using the speech analysis system 43. While the relatively small variation in stress may be expected for other individual security personnel when plotting stress level variability over time, this particular agent's measured stress levels were extremely consistent and always fell within a very narrow range, as analyzed by the program 110. Even though the measured stress level by the speech analysis system 43 at the time in question was within the required limits for access, the degree of variability fell outside of the expected range based upon his/her longitudinal analysis. This unexpected deviation as detected by the program 110, could in turn prompt the program 110 to provide an automated alert (via electronic means noted above) to security and compliance personnel within the agency, which could in turn trigger further and more detailed inquiry. Alternatively, since the speech analytics of the program 110 of the present invention provides a mechanism for longitudinal and historical analysis of the individual end-user's speech profile (i.e., personalized speech analytics), then the program 110 of the system 100 would automatically provide an automated alert to the appropriate parties, via electronic means as noted above, for the deviation in stress measurement relative to the security agent's historical profile, despite the fact that the measured stress level remained within an acceptable level. The ensuing response could include a number of interventions including (but not limited to) the following:

1. Detailed request for additional data referable to potential causes of increased stress (e.g., infection, external stressors, sleep patterns).
2. Automatic triggering of additional stress measurement tests.
3. Alert to security and compliance personnel notifying them of the data deviation.
4. Request for heightened electronic and/or physical surveillance of the individual agent.
5. Readjustment of user-specific stress measure requirements for future data access.

In yet another example, a pilot is required to undergo identification/authentication prior to performing his/her duties. The complexity of the tasks being performed by a pilot differs in accordance with a number of factors (including but not limited to) the duration of travel, technology in use, and weather conditions. As a result, the identification/authentication process of the program 110 of the present invention is expanded by the program 110 to incorporate "allowable" stress measures for the given context and individual user. An individual pilot's level of experience, past performance and safety records, emotional/physical state, and disciplinary actions could all be factored into the program 110 to determine the "acceptable" levels of stress for the task being performed. These "acceptable" levels for each individual end-user would in turn be affected by the difficulty in task performance (which would take into account the aforementioned factors of weather, technology being used, travel time, etc.). In the example of a complex task (e.g., night time flight in adverse weather conditions), analysis of the databases 113 by the program 110 could show which pilots have the highest performance records for the task to be performed and what each of their "acceptable" stress measures would be. The airline or military administrative officer could then check to see which of these pilots is available and then have them undergo speech analysis by the program 110 to determine the optimal candidate for selection. In this manner, the invention would simultaneously provide a dynamic tool for identification/authentication, technology for personalized comparative stress analysis, and decision support tool for performance optimization.

Another component of the present invention is the ability to perform real-time stress measurement, characterization, and analysis of speech. Although scientific works to date have documented the utility of speech analysis in the measurement and characterization of stress, the present invention is unique in that it requires adoption of a personalized speech profile for each individual end-user, which is created by the program 110 through the compilation of longitudinal speech analysis data. This personalized speech profile is in effect a speech signature for each individual end-user, which serves as an integral baseline for subsequent comparative stress analysis. A number of environmental, emotional, physical, occupational, and technologic factors can serve as sources of stress (i.e., stress modulators), which when compared by the program 110 with the end-user's personalized speech profile baseline, demonstrate stress-related speech changes. Examples of these stress modulators include elevated room temperature or humidity (environmental), loss of a loved one (emotional), infection (physical), change in job requirements (occupational), and implementation of a new technology (technologic). All of these produce changes from the individual end-user stress baseline and must be accounted for by the program 110 when analyzing occupational stress and fatigue upon task performance.

Taking the example of a physical stressor (e.g., infection), the end-user's measured stress/fatigue levels (i.e., blood pressure, galvanic skin response, etc.) would be expected to be elevated above baseline from the beginning of measurement by the stress measurement system 42, and continue to be elevated above baseline throughout the course of the day (assuming there is no significant change in infection severity). While the presence of this external stress inducer may or may not be documented by the program 110 during the course of stress measurements and analysis, the cross-referencing of "baseline" and "current" stress/fatigue data by the program 110 would clearly identify an incremental change above baseline, and in turn the program 110 would institute an adjustment in incremental analyses.

At the time of computer system 100 initiation (i.e. log-in), the end-user would be provided by the program 110 with a questionnaire attempting to gauge their emotional, physical, and cognitive states. If the end-user was to provide data which suggests an elevation in baseline stress (e.g., sleep deprivation, depression, or fever), the program 110, in performing stress analytics using stress measurement system 42, would take note of this and would automatically adjust subsequent analyses to reflect the expected and observed measurement fluctuation. If, on the other hand, the end-user did not provide input data to reflect a substantial change, the program 110 would recognize stress variations above the baseline (based upon quantitative measurements from stress measurement system 42 and speech analysis device 43) and automatically adjust the stress analytics in accordance with the global change in stress observed. The program 110 could also have a feature which prompts the end-user for additional data related to stress modulators, once the elevated baseline stress measures are recorded by the stress measurement system 42 and speech analysis system 43 and stored in the database 113. The ensuing stress analytics, feedback, and interventions could be adjusted by the program 110 to take into account these baseline changes, based upon the historical records of the individual end-user and end-users of similar profiles (i.e., peer reference groups).

The personalized speech profile is configured by the program 110 to be dynamic in nature and respond to periodic changes in both extrinsic and intrinsic stressors. Extrinsic stressors are external to the individual end-user and can be environmental (e.g., room temperature change), workload (e.g., task complexity or volume), or technical (e.g., technology being used), in nature. Intrinsic stressors are internal to the individual end-user (e.g., emotional state, illness) and can in part be accounted for by the various characteristics which define each individual end-user (e.g., age, gender, personality, education/training, work experience). While physical illness is not inherently a part of the individual end-user, the stress response to illness can to some extent be related to the individual end-user's profile. The program 110 having the ability to record, track, and analyze longitudinal stress data and correlate this data with the specific stressors for each individual end-user provides an objective mechanism for predicting stress variability in accordance with changing stressors, as well as creating stress intervention strategies.

Since technology plays a critical role in stress (both in positive and negative ways), the personalized speech stress profile analysis by the program 110 can also be used to better delineate the role individual technologies play in affecting stress, in accordance with the individual end-user and context of the tasks being performed. As an example, one physician who has a high technology proclivity and technology comfort level may have consistently low stress measures for a given task, when compared with a colleague who has a lower technology proclivity and technology comfort level. These different levels of "technology related" stress must therefore be accounted for in the personalized stress profile by the program 110. This "technology related" stress data can also be used by the program 110 to selectively adapt technology selection and modification in keeping with the individual end-user and task being performed.

As an example, an end-user with a low technology proclivity/high stress profile would be expected to be more susceptible to technology-induced stress and as a result may require a simpler version of a given technology than his/her high technology proclivity/low stress counterpart. The ability to utilize the personalized stress profile database 113, for the program 110 to effectively match the best technology option with each individual end-user, presents a mechanism with which extrinsic stressors can be modified in keeping with the performance characteristics of each individual end-user. In addition to technology selection, the same technology-stress analysis performed by the program 110, can be used by the program 110 to drive technology adaptability requirements for a single technology being used. For this application, a component of the technology such as the user interface, tools, or software program 110 being used, may be modified for the individual end-user in accordance with the measured stress levels and personalized stress profile.

The combined data of the stress analysis, personalized profile, tasks being performed, technology in use, and outcomes (i.e., performance), can collectively be analyzed by the program 110 to derive a user and context specific "stress inflection point". This is defined by the present invention as the specific stress measure at which objectively determined performance metrics deteriorate below an acceptable level. This uniquely defined "stress inflection point" is entirely derived from data analysis by the program 110, and can be dynamically adjusted by the program 110 in accordance with individual requirements, and can be calculated by the program 110 in accordance with the individual end-user profile, task being performed, and technology in use. Even though one end-user's performance metrics (e.g., diagnostic accuracy) may be superior to another colleague's performance metrics, the program-derived "stress inflection point" for each individual user is not static, but instead dependent upon each user's stress/performance data relationships. Since measured stress levels are dynamic in nature and subject to continuous changes in stressors, the stress inflection point serves as an important measure for which stress can be monitored and acted upon by the program 110 in keeping with a critical end-goal, yet also adjusted by the program 110 to each individual end-user's stress/performance record.

This stress inflection point is also dynamic and changes in accordance with the stress/performance metrics of individual tasks. As an example, a radiologist may exhibit higher performance measures for different exam types (e.g., CT angiography of the chest vs. magnetic resonance imaging (MRI) of the knee) at comparable stress levels, and therefore have different stress inflection points for each of these exam types. At the same time, the same radiologist may have different performance measures (at comparable stress levels) for the same exam type (e.g., chest CT angiography) but two different clinical indications (e.g., evaluate pulmonary embolism vs. thoracic aorta aneurysm). A final example might include the same radiologist, same exam type (e.g., chest CT angiography), and same clinical indication (e.g., pulmonary embolus). When using two different technologies (e.g., CAD programs) in performing interpretation, the same radiologist may have different performance metrics and/or stress level measurements; thereby creating two different stress inflection points. This illustrates the degree of granularity and specialization of the stress inflection point. The goal is to maximize performance outcomes (i.e., quality), provide data-driven feedback in real-time, maintaining flexibility in workflow, and utilizing the data for customized intervention strategies.

Another component of the present invention is the ability to use real-time stress analysis in speech, using a speech analysis system 43, to detect uncertainty and lack of confidence in decision-making and task performance.

While the previous components of the invention was focused on overall or generalizable changes in stress levels (e.g., due to cognitive overload), this component of the invention is aimed at detecting intermittent or narrowly focused stress, which would be specific to the task being performed. As compared with "generalizable" stress, these intermittent or "transient" stress fluctuations occur when an individual end-user experiences a temporary elevation in stress, related to an increase in task complexity. This transient increase in stress due to change in task complexity can be actual or perceived.

An example of an actual increase in task complexity can be illustrated in the course of a radiologist tasked with serial interpretation of medical imaging exams. When he/she transitions from a relatively simple and straightforward exam (e.g., chest radiograph for detection of pneumonia) to a more complex and data-intensive exam (e.g., MRI for re-evaluation of brain tumor following radiation therapy), one would routinely expect to observe a transient increase in measured stress levels, in accordance with the interval change in task complexity. On the other hand, if the same radiologist experienced a transient increase in measured stress when performing sequential interpretations on two imaging exams of comparable complexity, then an alternative cause must be the source of this comparative stress elevation. The presumptive cause for this transient stress elevation in the face of comparable (or less) task complexity would be stress associated with difficulty in performing the task at hand. In the example of a cognitive process such as interpretation of medical imaging studies, this transient stress elevation could be the result of indecision, lack of diagnostic confidence, or uncertainty in decision-making.

Simply stated, when a radiologist is confident and at relative ease in performing his/her duties, they would be expected to have lower stress measurements than the same radiologist who lacks confidence and becomes relatively uneasy (i.e., anxious) when performing a comparable task. The ability to detect these subtle transient changes in stress related to lack of confidence or uncertainty is dependent upon the ability to understand, quantify, and characterize the subtle nuances in speech for each individual end-user (i.e., personalized speech profile) and the ability to quantify and characterize task complexity.

Uncertainty analysis in speech could be accomplished in two (2) distinct ways. The first method would be the analysis by the program 110 of speech content for general and user-specific indicators of uncertainty. General measures of uncertainty might include use of vague and/or ambiguous language (e.g., "could be", "may be") or frequent use of filler terms such as "um" and "ah". User-specific language indicators of uncertainty would be derived from meta-analysis by the program 110 of an individual end-user report's content (using technology such as natural language processing) to identify repetitive patterns of content which have been shown to be associated with uncertainty and adverse outcomes for the specific end-user and task being performed. As an example, whenever a specific radiologist (i.e., Dr. Jones) is interpreting a chest CT, he will frequently use the words "bronchoscopy recommended as clinically indicated"; which is a unique manner in which he introduces uncertainty.

The second method for uncertainty detection in speech analysis utilizes methods similar to that used in lie detection (i.e., polygraphs). Examples of speech analysis used to detect deception include a higher pitched voice, slower speech rate, and a longer latency period. The ability of speech analysis by the program 110 to detect uncertainty (which is arguably a mild form of deception) is predicated upon the ability to create a user-specific speech profile over an extended period of use, which can take into account a number of contributing factors such as task complexity and baseline stress/fatigue. The program 110 uses intrinsic characteristics of speech to identify specific indicators of stress (which is distinct from baseline measures) which could serve to identify uncertainty in task performance. This uncertainty detected by the program 110 results in an "uncertainty prompt", which in turn is cross-referenced by the program 110 with the individual end-user's historical speech profile (specific to the task being performed) and outcomes indicators to identify instances of relative uncertainty and a potentially high probability for adverse outcome.

Thus, the premise to detecting uncertainty in speech through voice stress analysis is similar to lie detection examinations which have been reported to detect deception through identification of psychological stress in speech. While deception is generally thought of as a deliberate act to knowingly mislead, equivocations are also a form of deception, although in a far milder and less deliberate act. Equivocation employs the use of adjectives and adverbs in order to qualify the meaning of statements and introduce ambiguity and uncertainty.

A number of limitations exist in the use of voice stress analysis (VSA) for traditional lie detection, which are obviated by the present invention. These include the degree of inter-operator variability and subjectivity, ability for subjects to "game" the system, and lack of extensive baseline data relative to the subjects being evaluated. The "gaming" of the system has been well described by the use of physical (e.g., tongue biting) and mental (e.g., counting backwards) countermeasures subjects use when answering control questions in order to alter stress responses and confuse analysis of test questions. The present invention would counter these limitations through the use by the program 110 of objective computerized analysis of voice characteristics and stress, along with the creation of an in-depth personalized voice profile based upon longitudinal data collection over extended use of speech recognition.

In contrast to the issues present with lie detection, in order to detect subtle variations in voice stress and improve the accuracy of voice stress analysis, a personalized voice profile can be created by the program 110 for each individual end-user, which can be readily accomplished through the routine use of speech recognition technologies for medical reporting. Thus, the present invention moves past conventional speech recognition applications to create a personalized voice profile related to the unique elements of each end-user's voice and vocabulary, where the proposed speech analysis technology 43 would significantly expand the purview of these voice profiles by the program's 110 correlation of intrinsic voice characteristics with real-time stress measures using voice stress analysis. The resulting personalized voice-stress profile would create a personalized record depicting how an individual end-user's intrinsic speech characteristics change over time in accordance with changing measures of stress, workload, and task complexity.

By the program 110 correlating these data with performance outcome measures (e.g., diagnostic accuracy), the program 110 creates a method for predicting the relationship between stress-induced changes in voice, subconscious deception (i.e., uncertainty, lack of confidence) and task performance. Task performance can be analyzed by the program 110 by an assessment of the specific task being performed (e.g., exam type), complexity (e.g., size of dataset), clinical context (e.g., clinical indication), and quality measures (e.g., diagnostic accuracy). In the example of a radiologist tasked with interpretation of a brain MRI, the combined data could provide insight as to how the individual radiologist's speech characteristics and stress changed relative to baseline during the course of interpretation and reporting, how this compares with measures of different exam types and complexities, and how this correlates with outcome analysis (e.g., diagnostic accuracy based upon peer review or additional test results). This analysis could even be extended by the program 110 on a more granular level to assess uncertainty related to individual findings within a single report.

In addition to the program 110 measuring and analyzing periodic fluctuations in stress specific to context and individual user baselines, speech analysis could also be used to identify specific speech patterns associated with increased uncertainty such as such as hesitations in speech, increased frequency of specific (filler) words (e.g., "ums" and "uhs"), and longer latency periods. The end result would be a program-derived comprehensive speech analysis system 43 which identifies uncertainty through language (i.e., report content), speech patterns, and end-user specific voice stress variations.

In addition to analyzing uncertainty through speech analysis, a number of supporting technologies can be incorporated into implementation to improve performance. Two examples of these supporting technologies include uncertainty detection through linguistic and visual (eye-tracking) analyses. For linguistic analysis of uncertainty, natural language processing (NLP) can be used by the program 110 to identify terms of uncertainty and ambiguity introduced into the written report (e.g., "cannot exclude", "may be", "suggestive of"). For visual analysis of uncertainty, eye tracking technology (one of stress measurement systems 42) can be used to identify visual uncertainty which can take a number of different forms including increased dwell time and backtracking of eye movements over a single point of interest, and its data analyzed by the program 110. The goal of integrating these technologies with the program 110 would be to correlate uncertainty in different forms and use the supporting technologies to iteratively improve uncertainty detection and analysis in speech.

The ability of the program 110 to combine language and speech databases 113 for uncertainty detection and characterization could provide a synergistic mechanism for understanding how uncertainty is manifested in both context and user-specific fashions. As the individual language and voice stress uncertainty databases 113 identify elevated uncertainty measures, automated prompts can be sent by the program 110, via electronic means described above, to notify the end-user of the observation, along with statistical data relating the magnitude of and the measurement relative to baseline uncertainty measures. The corresponding uncertainty data can in turn be correlated by the program 110 with outcomes analysis data (e.g., diagnostic accuracy) to establish the relationship between uncertainty and quality specific to the context of the task being performed (e.g., clinical indication, exam type) and individual user.

Realizing that each individual end-user would have their own preferences as to how the uncertainty data would be communicated and acted upon, customized implementation pathways could be created by the program 110 to maximize technology adoption and integration into routine workflow. For example, radiologists may differ in accordance with how the uncertainty prompts would be communicated (e.g., visual versus auditory), when the action would take place (e.g., immediate versus end of task completion), the specific threshold which mandates an automated prompt, and intervention options (e.g., computerized decision support and data mining tools).

The ability of the program 110 to correlate uncertainty and outcomes data could potentially provide insights into the clinical significance of uncertainty and need for intervention. As an example, if quality assurance (QA) analysis of an individual radiologist's information stored in the database 113, by the program 110, shows a specific and reproducible stress (or language) uncertainty pattern associated with higher than expected QA discrepancies, then this user-specific voice stress pattern could be prospectively analyzed so that the program 110 will identify "high risk" reports (or individual findings) associated with inaccurate diagnoses. The ultimate goal would be the creation of a context and user-specific database 113 by the program 110 which could identify specific voice stress and language patterns associated with poor outcomes data. By the program 110 identifying these patterns in real-time, automated alerts and prompts could be sent by the program 110 to notify the radiologist of the concern, and present supporting data with present context-specific intervention options (e.g., computerized decision support, subspecialist consultations, and additional clinical data).

The ability to characterize task complexity in the practice of medical imaging has been described in U.S. patent application Ser. No. 12/137,926, filed Jun. 12, 2008, the contents of which are herein incorporated by reference in their entirety. An index of productivity workflow includes a mathematical model for quantifying task complexity based upon the expected time, workflow, and technology requirements for successfully completing a specific task. This methodology for quantifying task complexity may be integrated with the present invention, to incorporate changes in workflow and technology since each of these can serve as a source of stress. Thus, the program 110 can continuously account for variations in task complexity as it analyzes performance-related stress for each individual end-user and correlates these variations in stress with historical stress measures of the individual end-user.

While identification of uncertainty and anxiety related to a specific task is valuable, the determination of how this transient task-performance stress affects performance outcomes is important in order to establish a "cause and effect" relationship between uncertainty and lack of confidence with quality measures. Just because a radiologist may lack diagnostic confidence and exhibit uncertainty in establishing a diagnosis does not necessarily mean he/she is inaccurate in their diagnosis. If however, analysis of the stress and outcomes data by the program 110 does show a correlation (i.e., increased stress is associated with adverse outcomes), then positive outcomes can be effected by the program 110 identifying, communicating, and acting upon these transient increased stress levels at the point of care. Examples of potential intervention strategies instituted by the program 110 when the radiologist interpreting the medical imaging exams experiences a high level of stress in a specific task, could include the following:

1. Activation of computerized decision-support technologies (e.g., computer-aided diagnosis software).
2. Recommendation for a consultation or second opinion from a colleague.
3. Deferral of the case to another radiologist.
4. Bookmark of the case for subsequent quality assurance (QA) analysis and peer review.
5. Automated search by the program 110, of the patient's electronic medical record (EMR) for additional clinical/imaging data to assist in the interpretation process.

Clinical outcomes analyses are described in, for example, U.S. patent application Ser. No. 12/213,184, filed Jun. 16, 2008, Ser. No. 12/222,097, filed Aug. 1, 2008 (now U.S. Pat. No. 7,853,476), Ser. No. 12/, 11/699,344 8 filed Jan. 30, 2007 (now U.S. Pat. No. 7,301,461), Ser. No. 11/699,350 filed Jan. 30, 2007 (now U.S. Pat. No. 7,831,445), Ser. No. 11/699,348 filed Jan. 30, 2007 (now U.S. Pat. Nos. 7,532,942), and Ser. No. 13/403,529, filed Feb. 12, 2012, the contents of all of which are herein incorporated by reference in their entirety. The ability of the program 110 to query these clinical outcomes databases 113 in real-time, provides valuable feedback to the individual radiologist as to the likelihood of adverse performance outcomes in the face of uncertainty and lack of diagnostic confidence.

Two examples of brain MRI exams, where a given radiologist was alerted by the program 110 by electronic means (i.e., dialog box, text, email, etc.), to uncertainty and lack of diagnostic confidence in the course of image interpretation, are described below.

In one example, high levels of uncertainty were recorded by the program 110 in the database 113 for a case evaluating acute stroke, while in the second example, high levels of uncertainty were recorded by the program 110 in the database 113 for a case evaluating memory loss. In both examples, when unusually high levels of stress (relative to the radiologist's baseline profile and ongoing stress measurements) are recorded, an automated prompt is sent via electronic means, by the program 110, to alert him/her of the high stress and concern for uncertainty and lack of diagnostic confidence. This could be correlated by the program 110 with the linguistic content of the report being transcribed (using natural language processing software), in order to identify language in the report associated with uncertainty (e.g., "could be", "may be associated with", "cannot exclude"). The combined speech analysis and report language data would in turn be recorded by the program 110 in the stress database 113 for future analysis.

The speech analysis data (i.e., elevated stress measures) are correlated by the program 110 with the task complexity measures and context-specific clinical outcomes data in order to predict the clinical significance of the elevated stress levels (i.e., correlating with uncertainty and lack of diagnostic confidence). In the case of the brain MRI for stroke, the radiologist's historical outcomes data for stroke interpretation on brain MRI reports a diagnostic accuracy of 92% (for 112 prior cases). In the case of memory loss evaluation of brain MRI, the reported diagnostic accuracy is 99% (for 36 cases). When provided with this context and user-specific outcomes data by the program 110, the radiologist realizes that the uncertainty associated with the stroke case takes on greater importance than the uncertainty associated with the memory loss case, based upon his/her own historical outcomes data. As a result, the radiologist may elect to accept the memory loss report "as is" and not require additional intervention. For the stroke case with poorer outcomes results, the same radiologist may elect to seek out a second opinion from a colleague before finalizing the report. This shows the ability of the program 110 to support cross-analysis of the stress and outcomes databases 113 to determine the most effective course of action with the stress data being presented by the program 110 to the user.

The actions in response to the elevated stress measurements can be customized by the program 110 in accordance with the individual end-user (e.g., radiologist), department, or institution. As an example, one end-user may elect to continue performing all tasks despite feedback of elevated stress levels, whereas another individual end-user may elect to modify his/her workflow or temporarily stop working until stress levels return to baseline or more acceptable levels. Alternatively, the department or institution in which the end-user is employed may elect to have pre-defined rules which govern work under increased stress levels. These rules can be fixed for all end-users by the program 110, or can be modified by the program 110 in accordance with the specific task complexity and end-user performance metrics.

In the example of a modified stress protocol, the program 110, with a protocol approved by the institution, may determine that one end-user who has relatively high performance metrics under mildly elevated stress measures can continue to perform tasks of low to medium complexity, whereas another worker with lower stress performance metrics in the same job may be forced to discontinue work until acceptable stress levels are realized. This illustrates how operational rules and procedures of the program 110, regarding occupational stress and fatigue, can be modified (i.e., made flexible) in accordance with individual end-users' performance metrics and the complexity of task being performed.

One approach to address stress-related work performance issues, is to determine the specific inflection point at which performance metrics begin to degrade with elevated stress levels for each individual end-user and the specific task (complexity) being performed. Due to the fact that this inflection point is dependent upon the individual operator (i.e., inter-operator variability) and task complexity, it is important for the program 110 to utilize longitudinal user and context-specific data from the comprehensive stress analysis databases 113 for calculation of this inflection point (i.e., context and user-specific stress inflection point). The specific value of this inflection point could be easily adjusted by the program 110 in accordance with the "acceptable" stress levels determined by the individual end-user, department, or institution.

At some point in time, as industry-wide research expands, a community-based standard can be created by the program 110, in keeping with meta-analysis of the stress databases 113. In medicine, the creation of these best practices guidelines based upon meta-analysis of data is the heart of evidence-based medicine. The creation of these stress inflection points in medical practice can be calculated by the program 110 by determining the specific point in which quality standards begin to degrade and adversely affect pre-defined safety and quality goals. The advantage of this approach is that individual end-user performance is taken into account by the program 110, as opposed to creating hard and fast stress standards which are inflexible. Simply stated, the ability for different end-users to maintain acceptable quality and safety levels is highly variable in accordance with the context (i.e., task being performed) and user.

Another unique advantage of creating these data-driven stress inflection points is that they are dynamic in nature, and are continuously updated and revised by the program 110 as additional data is recorded and analyzed in the database 113. As a result, a specific end-user (e.g., pilot) who has recently experienced changes in performance measures (e.g., due to a new visual, emotional, or physical impairment) would have an adjusted stress inflection point to account for recent performance changes, as opposed to traditional method of adjusting data requirements and calculations on an annual basis.

An additional attribute of the present invention is the ability of the program 110 to retrospectively link adverse performance measures to specific speech analysis patterns, which may or may not have been identified by the program 110 through prospective uncertainty measures. As an example, quality deficiencies may be identified by the program 110 during the course of evaluating a task which was performed using speech. For a physician, this may include a dictated operative (or other procedural) note, history and physical, discharge summary, or test result. For law enforcement or military personnel, this may include a recording of a verbal communication or directive which ultimately led to an adverse outcome. For a pilot, this may include speech input used to direct navigation and in-flight adjustments. Regardless of the occupation and specific use, retrospective speech analysis by the program 110 may identify specific speech patterns or components within speech which are associated with negative outcomes. Upon further review by the program 110 of the speech analysis database 113, the program 110 could identify user and context specific patterns of speech which have a strong association with negative outcomes. This retrospective analysis by the program 110 can, in turn, be incorporated into prospective speech analysis by the program 110, to identify those speech patterns with a statistically higher incidence of performance degradation. The associated statistical data specific to the context and individual user can in turn be presented by the program 110 at the time of speech delivery, to alert the end-user in the same manner in which real-time speech analysis is used by the program 110 to alert an end-user of high stress and/or uncertainty levels. This illustrates how the program 110 can be used to improve performance and quality both through prospective and retrospective data analysis.

An internal quality assurance (QA) mechanism can be incorporated into the program 110 to ensure that individual end-users are not routinely ignoring stress data feedback and continuing to perform their duties in a manner which adversely affects performance and safety. While the specific parameters for determining when these QA triggers would be initiated can be customized by the program 110 in accordance with individual preferences, the ultimate functionality and accountability of the present invention would remain consistent. Whenever an individual end-user continues to operate in a manner considered to be unacceptable (based upon a comparison analysis by the program 110 with the predetermined stress inflection data), an automated alert would be sent by the program 110 to the end-user, using electronic means, with the recommendation to temporarily cease or modify workflow. The various intervention options would be presented to the end-user by the program 110, in accordance with his/her pre-defined preferences (which have been described in, for example, U.S. patent application Ser. No. 13/537,976, filed Jun. 29, 2012, the contents of which are herein incorporated by reference in their entirety). If the end-user continues to work/operate, and recorded stress levels do not decrease to pre-defined acceptable levels, an automated, QA alert is sent by the program 110 by electronic means, which triggers a notification pathway to designated parties (e.g., department chief, chief information officer, compliance officer, chief operations officer). In addition, the existing QA protocol would be accelerated by the program 110, to review all data during the "higher than acceptable stress" period of operation.

In the example of a radiologist tasked with interpreting medical imaging exams, all exams interpreted during the period of "unacceptable high stress" would be tagged by the program 110 to be subjected to formal QA and peer review. This provides a mechanism to ensure that "high-risk" work is carefully scrutinized for quality and safety, and appropriate interventions can be immediately performed to minimize the risk of adverse outcomes. Individual end-users who continuously ignore these stress alerts may be subject to, not just computer system 100 suspension or lockout, but disciplinary action, which could range from a mandatory in-service, work suspension, or termination.

Each time an end-user discontinues or ceases work, an automated speech analysis would be performed by the program 110. This serves to document the specific level of stress at the time of work termination and increase expansion of the individual end-users' identification/authentication speech analysis database 113. Since speech analysis of stress takes place under two separate conditions (continuous speech during active work and targeted speech during identification/authentication), it is essential that the speech analysis is able to differentiate stress measures under these different speech patterns.

In order to expand the identification/authentication speech database 113, the end-user would be prompted with predefined text to speak prior to discontinuing or terminating work. The specific text presented would be randomly generated from a large and continuously changing list of statements from the database 113, in order to prevent the end-user from "gaming" the system and intentionally modifying their speech patterns, in an attempt to modify the recorded stress levels. The analysis of this targeted speech by the program 110 could in turn be correlated with stress measurements recorded and stored in database 113, in continuous speech usage immediately prior to work termination. This provides a method for directly correlating stress measurements in speech for both continuous and targeted methods of speech.

Another unique feature of the present invention which is directly tied to its longitudinal database 113, is the ability of the program 110 to provide quantitative measures of statistical probability with each form of data output. This provides the end-user (and other parties of interest) with a mathematical probability that the presented data is accurate and reproducible. As one would expect, these statistical probability measures by the program 110, are directly tied to the sample size of statistical analysis and ability to correlate the predictive data elements with outcome data, which in effect established truth. Early on in the process of speech analysis implementation by the program 110, the individual end-user would expect these probability measures to be modest, and over time as the sample size of available data increases, so would the corresponding probabilities. Once this technology is validated through longitudinal analysis by the program 110, these measures can be used to assist the technology users in establishing protocols and patterns of use.

As an example, an institution may create a policy that statistical probabilities greater than 98% are to be accepted by end-users as accurate and reproducible and resulting workflow and QA actions must be followed in accordance with institutional protocol, and the program 110 is programmed accordingly. On the other hand, the program 110 would be programmed that statistical probabilities <95% are of low enough probability that the end-user has greater latitude in how he/she utilizes the data in their task performance and workflow modifications. The end-result is that these probability measures provide a data-driven mechanism for the program 110 to establish "best practices" standards and serves to improve acceptance and validation of the technology.

The personalized speech analysis profile of the program 110 of the present invention creates a reproducible tool for characterizing end-users (profiles) in accordance with numerous factors which define their occupational, personal, language, and technical attributes—such as, demographics, education and training, work experience, personality, emotional state, sensory and motor skills, intelligence, technology proclivity, and linguistics). The personalized speech analysis profile follows the end-user wherever he/she goes and can be linked directly by the program 110 to their identification/authentication (which is also an important component of the invention), through a centralized database 113 which stores, analyzes, and correlates the various data elements within the speech analysis profile, as performed by the program 110. This end-user specific profile is continuously updated by the program 110 as new and continuous data is recorded in the database 113, making it dynamic in nature. Relevant examples to illustrate how this profile would be modified over time by the program 110 include (but are not limited to) changes in technology proclivity as new/additional computer skills are learned, changes in linguistics as an end-user modifies his/her speech patterns and content, continued occupational education and training programs which modify knowledge and skill sets, and emotional changes which occur as a response to situational and/or personal life changes.

While a number of benefits can be derived from this personalized profile, perhaps the most important is the ability of the program 110 to create peer reference groups, which can categorize individual end-users into groupings of "similarity", which in turn can be used by the program 110 for interpersonal interactions between users sharing common attributes, creation of profile-specific "best practices" guidelines, research, and creation of adaptive technologies which are designed to play to the unique strengths and deficiencies of collective end-users.

These personalized speech analysis profiles would be created by first, having the program 110 request that individual end-users submit data from a standardized questionnaire which tracks standardized data related to the various data categories, as noted above, such as demographics, education and training, work experience, personality, emotional state, sensory and motor skills, intelligence, technology proclivity, and linguistics, which is then stored in the database 113. It is important that the data being recorded by the program 110 in the database 113 is standardized, thereby providing a mechanism for meta-analysis by the program 110 using large-scale multi-institutional statistics. While some of this standardized data can utilize existing instruments (e.g., NEO-Personality Profile), others would be created by the program 110 (i.e., standardized rating system for classifying technology proclivity). The collective data derived from this standardized questionnaire would then be used by the program 110 to categorize individual end-users into groups based upon analyses of the data categories noted above, along with a composite score. The standardized questionnaire would be presented by the program 110 to the end-user on a periodic basis (i.e., every 3 months) to assess interval change in profile data, which would also be supplemented by ongoing data analysis by the program 110 (i.e., natural language processing of text reports to assess changes in linguistic content).

In conjunction with the creation of the personalized speech analysis profile by the program 110, each individual end-user must be registered into the various speech analysis databases 113 as to their unique identity and authentication pathway. (The various components and functionality of this identification/authentication process has been described in, for example, U.S. Pat. No. 7,593,549, the contents of which are herein incorporated by reference in their entirety.) Since the creation of a unique speech analysis "signature" by the program 110 requires validation and longitudinal analysis, ancillary biometrics identification technologies 41 would be incorporated into the process by the program 110. As an example, when an individual end-user registers, different biometrics technologies 41, biometrics data would be used by the program 110 to establish their unique identity, which in turn would be correlated with their speech analysis "signature". Examples of the various speech analysis components used by the program 110 to create this user-specific speech signature include, for example: pitch amplitude, and distribution, duration, frequency characteristics, mean articulation rate, spectral content, structure and intensity, glottic source factors, and depth and rate of modulation.

As noted above, each individual end-user's speech analysis signature is divided by the program 110 into two distinct components; which are derived from continuous speech (e.g., when performing a task such as report creation) and targeted speech (e.g., speaking a pre-defined string of text). For the initial creation of the speech analysis signature, the program 110 would randomly select a number of word strings or sentences for the end-user to say, and record his/her speech in the database 113 for subsequent analysis. As noted above, the speech analysis database 113 may contain thousands of these strings which provide a reliable mechanism for the program 110 to ensure that the end-user is constantly being exposed to new and different word strings for analysis, which acts to prevent "gaming" of the speech analysis system 43.

In addition to this initial registration process, each individual end-user would regularly be asked by the program 110 to input additional targeted speech data during the course of everyday task performance, which serves as a mechanism to continuously record additional data in the database 113 for speech analysis, quantify subtle changes over time, and provide a mechanism to for the program 110 to correlate continuous and targeted speech analysis for stress measures. This latter feature is important in order for the program 110 to be able to characterize stress and fatigue at the time each individual end-user undergoes the identification/authentication process by the program 110.

At intermittent times during routine task performance, the program 110 would prompt the end-user to input speech from a randomly selected text string (i.e., targeted speech). The analysis of this targeted speech string would then be used by the program 110 to measure stress in correlation to the recently measured stress using continuous speech. The presentation of these targeted speech strings by the program 110 can occur at periodic intervals of task performance (e.g., hourly) and as noted above, at the conclusion of work (i.e., closing folders, or request for computer sign-off).

During registration, in which the end-user identification and authentication is instituted by the program 110, a brief standardized data questionnaire would be presented to the end-user by the program 110, for the purposes of assessing various physical and emotional factors (i.e., stress modulators) which influence stress (e.g., sleep quality, restfulness, emotional state, physical well-being). This stress modulator data is correlated by the program 110 with the speech analysis data during registration and continued task performance, in order to more accurately determine the relationship and predictability of individual end-user stress measurements over time. As an example, during the identification/authentication process, an end-user reports that he/she is overly tired due to a sinus infection and poor quality sleep (which is reported using a standardized grading system). The resulting stress modulator score compiled by the program 110, which is a composite of the individual stress modulators contained in the survey questionnaire, would in turn be correlated by the program 110 with historical speech analysis of the individual end-user, in order to more accurately predict baseline stress as well as expected changes in stress over time. As the speech analysis database 113 becomes richer in data, the program-derived speech analysis of stress, and accuracy of end-user identification/authentication, increases. Whenever a question of accuracy in identification/authentication was to take place, the program 110 would leverage alternative biometrics technologies 41 (which data are also contained in the database 113) for improved accuracy. This provides an effective safeguard to ensure accuracy and reproducibility of the speech analysis data.

The manner in which real-time stress and fatigue is recorded, analyzed, presented, and interventions made by the program 110, are described in U.S. patent application Ser. No. 13/537,976, filed Jun. 29, 2012, the contents of which are herein incorporated by reference in their entirety. The major factor in real-time stress and fatigue analysis of speech is that it is designed to measure stress in a generalizable manner by tracking gradual changes in stress/fatigue over time and correlating these measures with defined operational limits. If/when the measured stress/fatigue exceeds a pre-defined threshold (which is dependent upon the individual end-user and task being performed), as analyzed by the program 110, an automated prompt issued by the program 110 via electronic means, will alert the end-user of the elevated stress measure and provide a series of intervention options in keeping with the task being performed, magnitude of the stress/fatigue measure, and individual end-user preferences.

An additional novel feature of the present invention is the real-time analysis of uncertainty and confidence in decision-making and task performance by the program 110. Unlike the aforementioned real-time generalizable stress measurement tool and analysis by the program 110, this application is intermittent or incremental in nature due to the fact that degrees of uncertainty and confidence are by definition, constantly changing. This uncertainty analysis can be performed by the program 110 on a comprehensive or partial (i.e., task by task) basis.

As an example, when evaluating uncertainty in the interpretation of medical imaging exams by a radiologist, characterization of uncertainty can be measured by the program 110 for the entire imaging report or for individual findings contained within the report. The best way to illustrate these differences in generalizable and incremental stress measures is to consider these two stress measurements over time. The deviations in generalizable stress measures tend to be gradual and additive over time, with subtle variability in accordance with changes in task complexity. The deviations in incremental stress measures related to uncertainty and confidence in decision-making tend to be more volatile in nature. If one was to subtract the generalizable stress changes in accordance with task complexity from the stress changes related to uncertainty, one would be left with a task by task measure of end-user uncertainty, which can in turn be included as a component of the individual end-user stress profile.

Figure 2A:
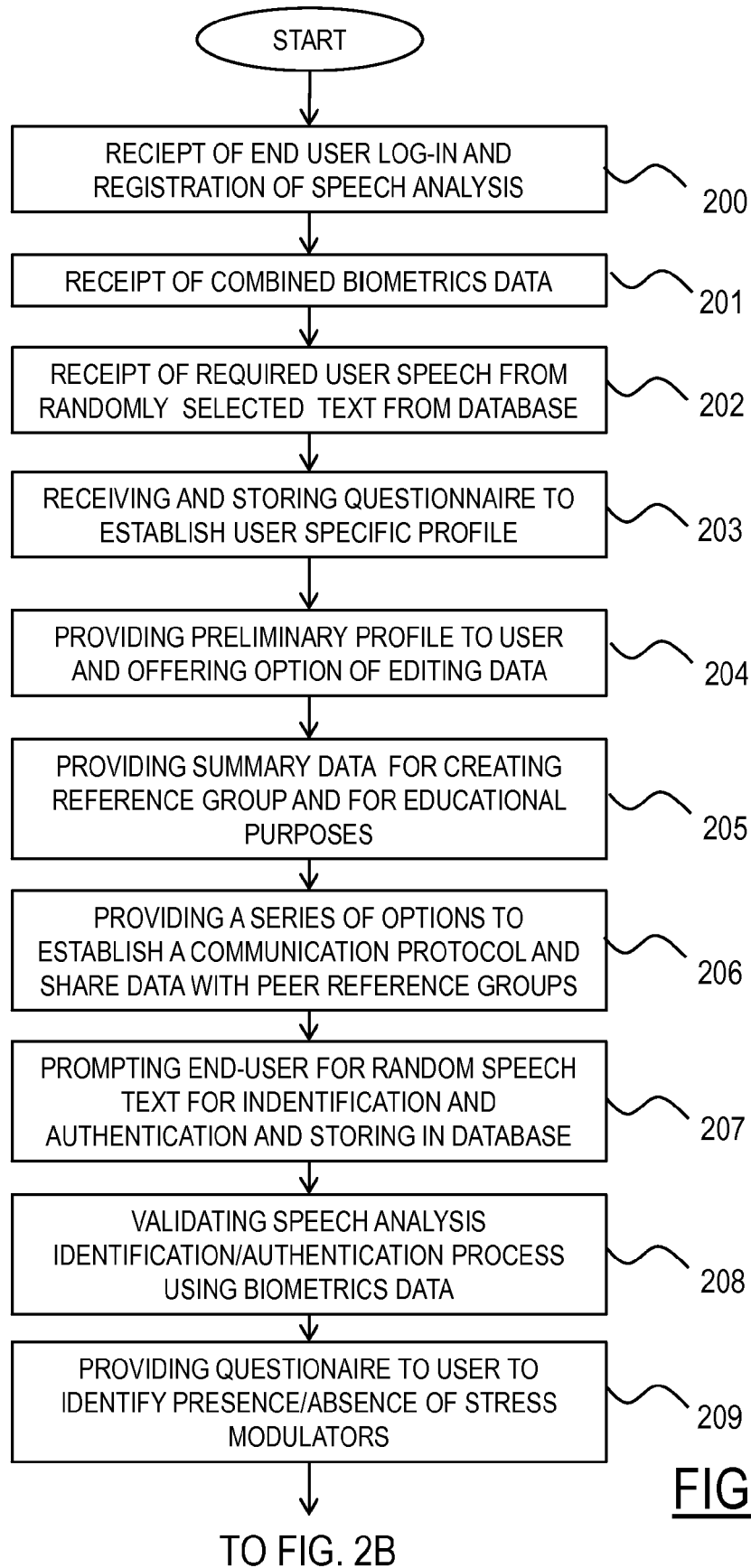
FIG. 2A-C are flowcharts of the steps involved in performing speech analysis to provide real-time measurement of end-user stress, fatigue, and uncertainty, according to one embodiment consistent with the present invention.
Figure 2B:
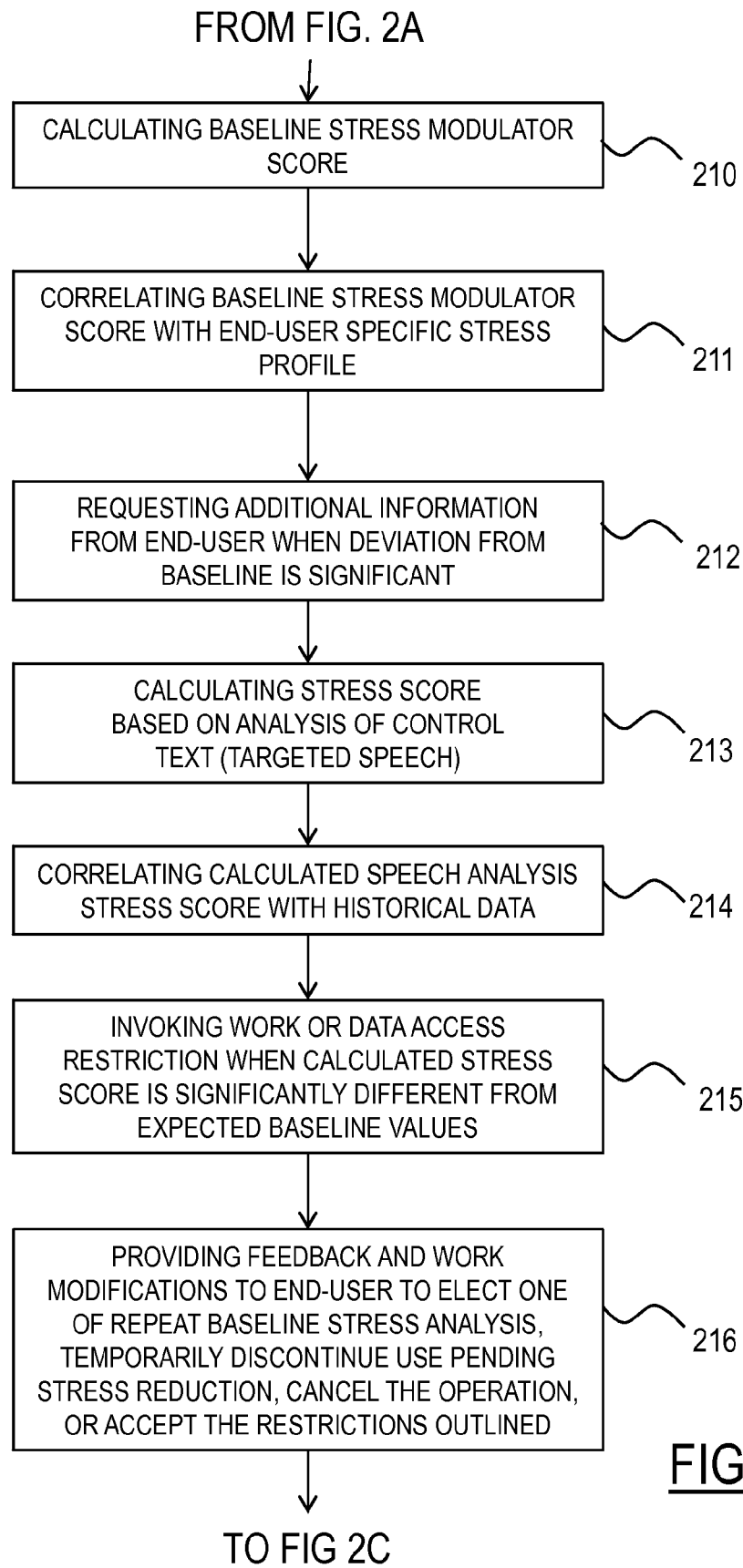
Figure 2C:
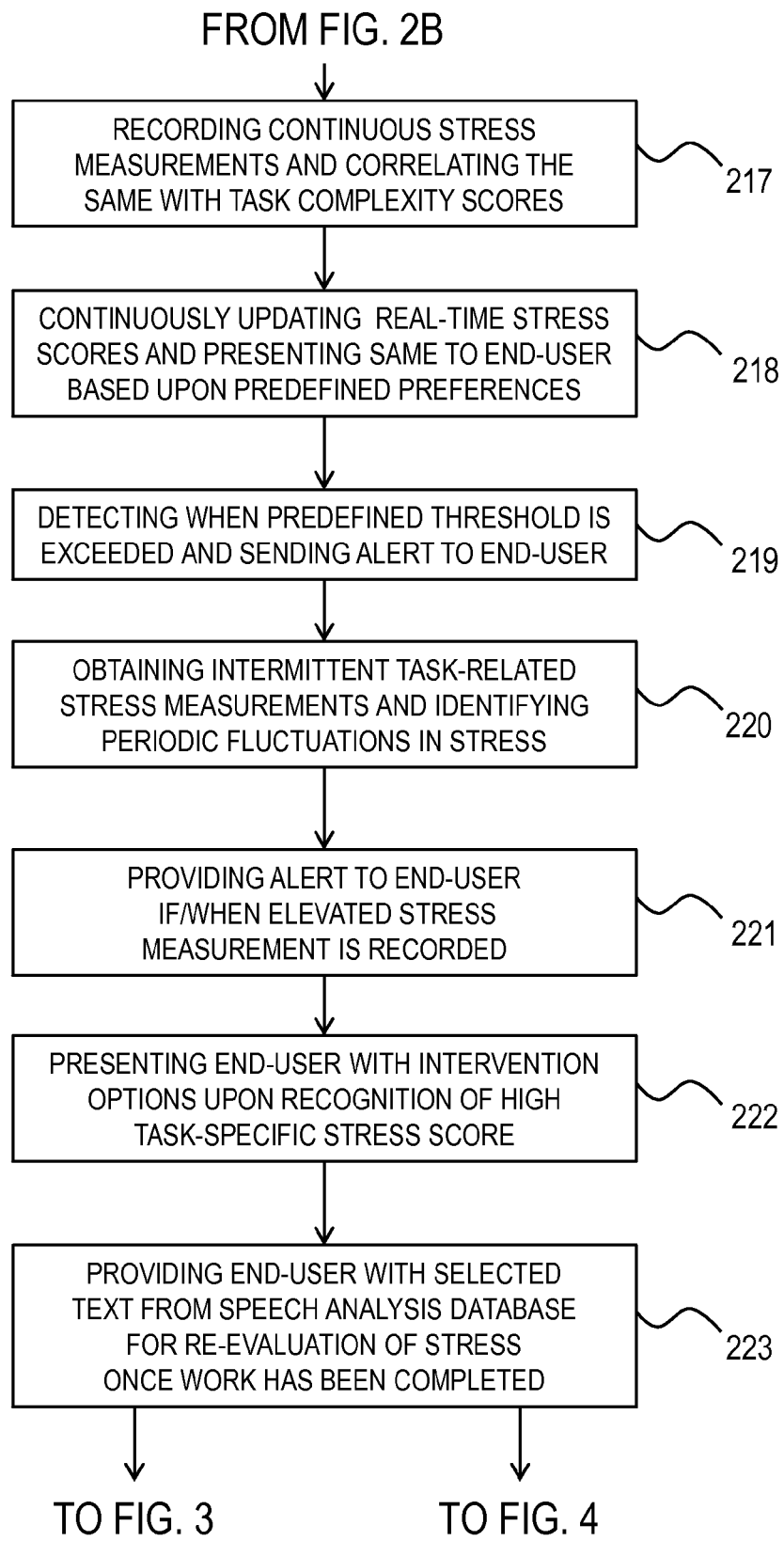

To illustrate how these various components of the invention work, the following flow charts demonstrate the various functionalities and applications of the invention. For this example, a radiologist tasked with interpretation of medical imaging exams, and the speech analysis to provide real-time measurement of end-user stress, fatigue, and uncertainty in decision-making, is described with respect to FIGS. 2A-C.

In step 200, at registration, an end-user logs into the computer system 100, and the program 110 receives a request for registration for speech analysis.

In step 201, the program 110 requires and receives, from the end-user, combined biometrics data (e.g., retinal scanning) from the biometrics system 41.

In step 202, the program 110 presents and requires the user to say randomly selected text from the speech analysis database 113), so that user-specific identification can be established in combination with the combined biometrics.

In step 203, the program 110 presents a questionnaire presented to the end-user for establishing a user-specific profile, and receives and stores the provided data.

In step 204, after completion of the baseline questionnaire, the program 110 presents the user with a preliminary profile and offers an option to the end-user of editing the data prior to assignment of a peer reference group.

In step 205, the program 110 provides summary data illustrating how a reference group was created, and shared characteristics stored in the database 113 for educational purposes.

In step 206, the end-user is provided with a series of options used to establish a communication protocol and the sharing of data with other peer reference group members.

In step 207, in routine use, the end-user begins work, and is prompted by the program 110 with a series of randomly selected text strings from the speech analysis database 113 (targeted speech) for identification and authentication, which speech is stored in the database 113 for further analysis.

In step 208, the speech analysis identification/authentication process is externally validated with biometrics data by the program 110, which is stored in the user-specific speech analysis database 113, and such validation confirmed to the user.

In step 209, the program 110 presents a standardized questionnaire to the user to identify the presence or absence of stress modulators, and the data stored in the database 113.

In step 210, based upon the answers to these questions, the program 110 calculates a baseline stress modulator score which quantifies the degree of expected baseline stress.

In step 211, the program 110 correlates this baseline stress modulator score with the user-specific historical stress profile to identify changes above or below baseline.

In step 212, if a significant deviation from baseline is detected by the program 110, additional information related to stress modulators is requested from the user for clarification and correlation with actual stress measurements, and stored in the database 113.

In step 213, after completion of the preliminary speech analysis for end-user identification/authentication process by the program 110, the program calculates a stress score based upon analysis of the control text (targeted speech).

In step 214, this calculated speech analysis stress score is correlated by the program 110 with historical data stored in the speech analysis database 113.

In step 215, if the comparison by the program 110 of the calculated stress score is significantly different from the historical, expected baseline values, the program 110 may invoke work restrictions or data access restrictions, in accordance with institutional and departmental policy.

In step 216, based upon this feedback and work modifications by the program 110, the end-user may elect to one of: repeat the baseline stress analysis, temporarily discontinue use pending stress reduction, cancel the operation, or accept the restrictions outlined.

In step 217, once workflow begins again, continuous, real-time stress measurements are recorded by the program 110 in the database 113 from the stress measurement device 42 and speech analysis device 43, and the program 110 correlates the stress measurements with task complexity scores (which can be calculated by the program 110 using computerized measures (see, for example, U.S. patent application Ser. No. 12/137,926 filed Jun. 12, 2008, the contents of which are herein incorporated by reference in their entirety).

In step 218, these real-time stress scores are continuously updated by the program 110 and presented to the end-user based upon his/her pre-defined preferences for data presentation.

In step 219, in the event that the continuous stress scores (based upon speech analysis) exceed a pre-defined threshold as detected by the program 110, then an automated prompt is sent by the program 110 via electronic means, to alert the end-user of the elevated stress scores along with intervention options.

The calculation of this stress threshold is the result of combined data related to the individual end-user profile, historical stress measurements, task complexity, and outcomes analyses. (The outcomes analyses provide an objective means to determine the cause and effect relationship between stress levels and performance metrics (e.g., diagnostic accuracy).

In step 220, in addition to continuous stress measure calculations, the program 110 obtains intermittent task-related stress measurements through real-time speech analysis to identify periodic fluctuations in stress related to uncertainty and confidence in task performance.

In step 221, if and when an elevated stress measure is recorded in the database 113 (relative to the baseline stress measure at that particular time), an automated prompt is provided by the program 110 to alert the end-user of stress elevation and the specific task (i.e., point in time in which this stress measure was recorded). In the example of the radiologist interpreting a medical imaging exam (e.g., MRI of brain), an electronic time-stamp is recorded which identifies the specific action in which the elevated stress measure is recorded. For this example, the specific action recorded by the program 110 could consist of the specific image, annotation, and/or recorded text associated with the elevated stress measure. The combined stress data related to uncertainty is recorded in the corresponding speech analysis database 113 by the program 110, for future review and analysis, specific to the individual end-user, task performed, data reviewed, and outcomes. If and when a similar task is presented to the same end-user in the future, an automated prompt by the program 110 will alert the end-user as to the fact that elevated stress and uncertainty were previously recorded for a similar task.

In step 222, upon recognition of the high task-specific stress score (relative to baseline), by the program 110, the end-user is presented by the program 110 with a number of intervention options. These may include (but are not limited to), for example, a request for a formal consultation (i.e., second opinion), use of computerized decision support (e.g., CAD), request for additional data (e.g., clinical data in the patient's EPR), or request to release the case and defer to another party. Elevated stress scores (both continuous and incremental) which exceed a pre-defined threshold, automatically trigger an advance QA analysis by the program 110, which calls for in-depth analysis by the program 110 of the data and task performance. For radiology interpretation this may consist of detailed and more frequent peer review, clinical outcomes analysis, or review by a QA specialist.

In the event that elevated stress scores are found to be associated with poor outcomes by the program 110, a QA committee may recommend that restrictions be placed on the end-user related to restrictions of task complexity, mandatory stress interventions, or remedial education/training.

In step 223, once work has been completed and the end-user requests to log out of the system, or closes folders related to the task etc., the program 110 will provide the user with selected text from the speech analysis database 113 for re-evaluation of stress, which the program 110 then correlates with recent stress levels measured in task performance using continuous speech. Thus, the present invention utilizes real-time measurement speech analysis of end-user stress, fatigue, and uncertainty in decision-making.

Figure 3:
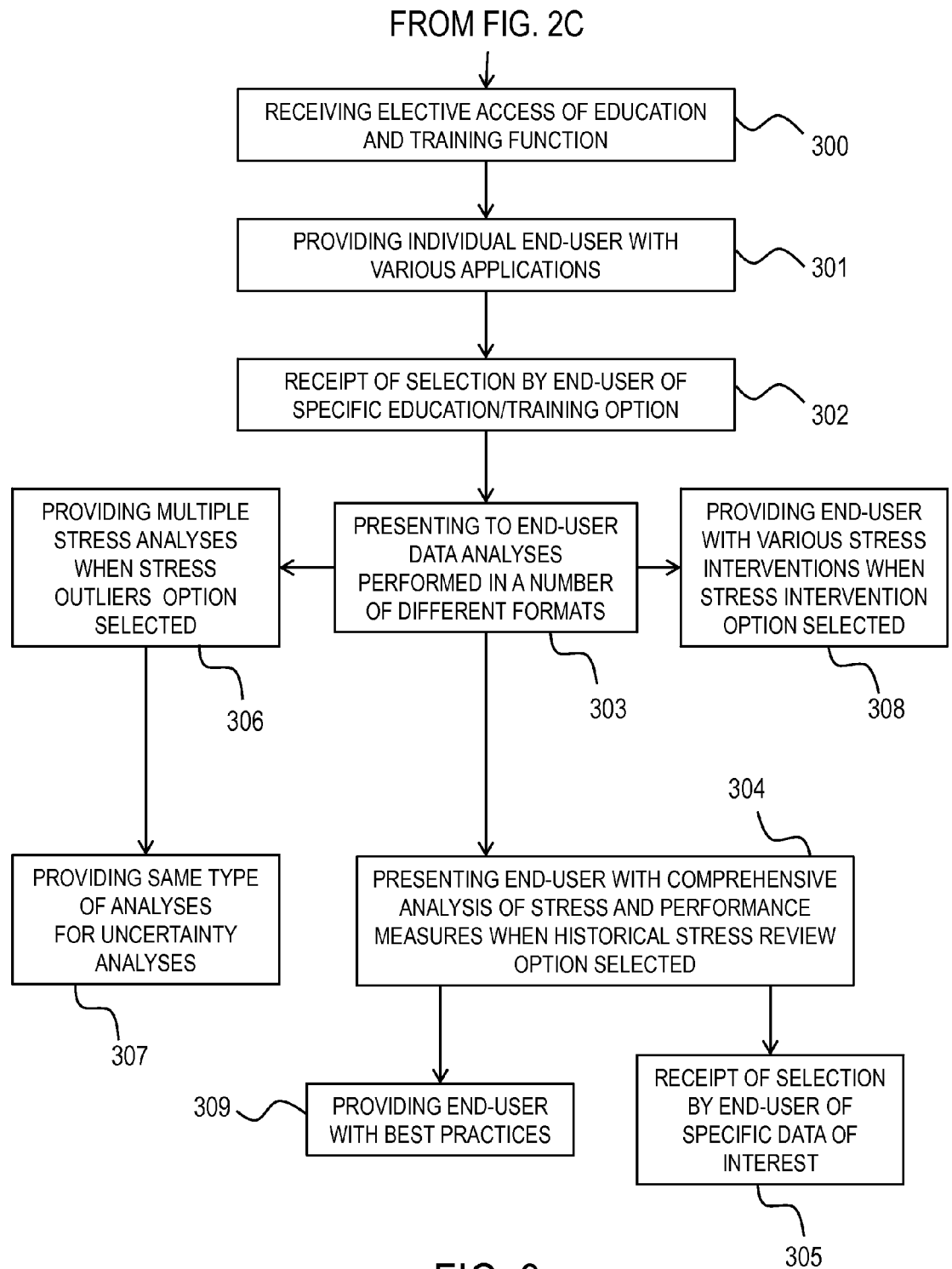
FIG. 3 is a flowchart which shows an education and training feature of the invention of FIG. 2.

In one embodiment, the present invention includes an education and training feature, which is described as follows, with respect to FIG. 3.

In step 300, the program 110 receives elective access of the education and training function of the program 110 after user identification and authentication by the program 110. Alternatively, the education and training function can be automatically invoked by the program 110 at pre-defined time intervals or in the event of a critical action.

In step 301, once the education and training function has been activated, the program 110 will provide the individual end-user with a number of applications including historical stress review, stress outliers, uncertainty, stress interventions, and best practices.

In step 302, when selectively used, the end-user may select the Education/Training option of specific interest.

In step 303, once opened by the program 110, the corresponding data analyses performed by the program 110 will be presented to the user in a number of different formats (graphical, numerical, and textual) which can be selected by the user for presentation based upon individual preference (these preferences can also be automatically applied based upon selected end-user defaults).

In step 304, when the Historical Stress review option is opened by the user, the program 110 presents the end-user with a comprehensive analysis of stress and performance measures based upon his/her unique data, along with comparable data from similar end-users (i.e., similar profiles).

In step 305, whenever specific data is of interest to the end-user, the end-user can select the specific data point of interest and the program 110 will provide a detailed analysis including tagged data, for review.

In step 306, the program 110 may receive user selection of the Stress Outliers option, and the program 110 will provide multiple stress analyses which: incorporate data related to daily baseline stress measures, variability in stress modulators, periodic stress variability, and relationships of stress measures to task complexity, workload, and outcomes measures.

In step 307, the program 110 provides the same types of analyses for Uncertainty analyses, except that these stress analyses focus on the frequency and specific circumstances in which elevated uncertainty stress measures are recorded (as opposed to continuous stress measures).

In step 308, when Stress Interventions is selected by the end-user, the program 110 will provide the end-user, for review, various stress interventions, impacted stress measures, the relative success or failure of different intervention options specific to the specific type of stress and task being performed, and how stress interventions of the end-user compares with those of similar end-users within his/her profile group.

In step 309, the program 110 will provide the end-user with Best Practices, with his/her stress analysis and performance data in comparison with those individuals within the same profile group which recorded the most efficient, high quality, and lowest stress measures. The various tools and options utilized by these "best performers" will be presented to the user by the program 110, for user review, along with the specific context in which they were utilized.

Figure 4:
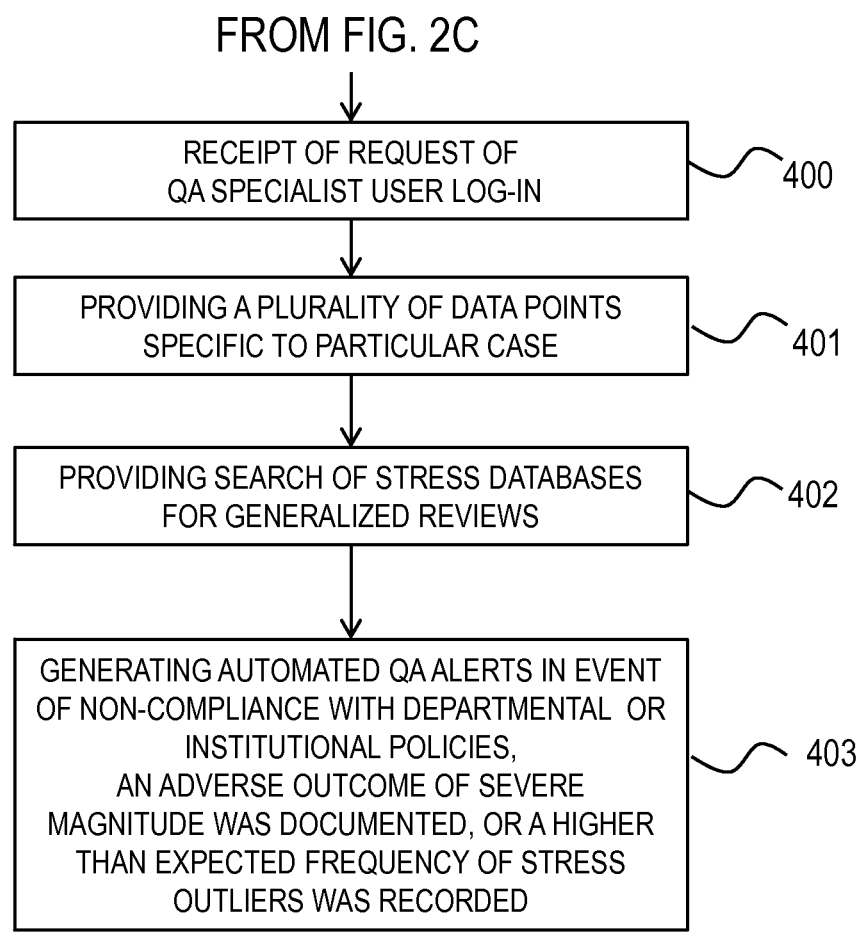
FIG. 4 is a flowchart which shows a feature for quality assurance and administrative oversight with respect to the invention of FIG. 2.

In one embodiment, the present invention includes a feature for quality assurance and administrative oversight (see FIG. 4), where whenever QA review or administrative oversight is required (which may be based upon departmental policy or performance indicators), the stress analysis databases 113 can be used by the program 113 to provide individual, departmental, or community wide statistical analyses.

In step 400, for a targeted QA review (i.e., specific case with adverse outcome), the QA specialist or administrative officer would first log into the system 100 and if properly credentialed and authenticated by the program 110, can proceed to access the QA functions of the program 110.

In step 401, the QA specialist is provided by the program 110 with a number of data points specific to the case in question, including (but not limited to) the end-user identity, task performed, measured stress levels at the time of interest (which could include baseline, periodic, and targeted stress measures), uncertainty measures, feedback presented, intervention options employed, and outcomes data.

In step 402, for generalized reviews, the QA reviewer could search the stress databases 113 based upon a large number of variables for the purposes of trending analyses, technology performance, tasks performed, collective and individual stress measures, and comparative analyses relative to large population based statistics.

In step 403, the program 110 will generate automated QA alerts in the event that an end-user did not adhere to departmental or institutional policies regarding stress response and interventions, an adverse outcome of severe magnitude was documented by the program 110, or a higher than expected frequency of stress outliers was recorded by the program 110 in the database 113.

Thus, based on the foregoing, the present invention provides speech analysis to provide real-time measurement of end-user stress, fatigue, and uncertainty in decision-making.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method of measuring speech for stress, fatigue and uncertainty, by a user of a computer system, comprising:

providing a speech analysis device into which a user is directed by a computer system, to speak random text retrieved from a database and shown on a computer display;

obtaining user-specific identification related to user speech, which is used in conjunction with identification of said user, to provide identification and authentication data of said user;

providing a questionnaire to said user, to obtain data to establish a user-specific profile, and storing the provided data in said database;

providing targeted speech to said user on a computer display, as a series of randomly selected text strings retrieved from said database, for the user to speak into said speech analysis device for speech analysis identification and authentication, and after validating of said user, storing said targeted speech data in said database for analysis; and obtaining intermittent stress measurements from said user during a task, through real-time speech analysis using targeted speech;

wherein after completion of said speech analysis for identification and authentication of said user, said speech analysis identifies fluctuations in stress measures caused by stress, fatigue, and uncertainty of said user; and calculating a stress score for said user based upon said speech analysis.

2. The method according to claim 1, further comprising:

providing a standardized questionnaire to the user to identify one of the presence or absence of stress modulators; and storing said data from said standardized questionnaire, in said database.

3. The method according to claim 2, further comprising:

calculating a baseline stress modulator score to analyze and quantify a degree of expected baseline stress of the user; and correlating said baseline stress modulator score with a user-specific historical stress profile to identify changes above or below a baseline stress measure.

4. The method according to claim 3, further comprising:

detecting a deviation from said baseline stress measure;

requesting additional information related to said stress modulators from the user for clarification and correlation with actual stress measurements; and storing said additional information in said database.

5. The method according to claim 3, further comprising:

correlating said stress score with data in said user-specific historical stress profile, and when said stress score differs beyond a predetermined threshold, invoking work restrictions or data access restrictions on the user in accordance with predetermined institutional and departmental policy;

wherein said predetermined threshold can be adjusted in accordance with said user-specific historical stress profile.

6. The method according to claim 5, wherein based upon said work restrictions or data access restrictions, receiving instructions from the user to one of repeat the baseline stress analysis, temporarily discontinue use pending user stress reduction, cancel work, or accept said work or data access restrictions.

7. The method according to claim 5, further comprising:

continuously updating said real-time stress scores, and presenting the user said updated stress scores based upon user pre-defined preferences for data presentation.

8. The method according to claim 7, further comprising:
recording continuous stress measurements, in real-time, to the database from a stress measurement device and said speech analysis device during tasks by the user; and
correlating said stress measurements with task complexity scores, said user-specific profile, said user-specific historical stress profile, and performance outcomes analysis.

9. The method according to claim 8, wherein when an elevated stress measure is recorded to said database during said task, relative to said baseline stress measure at that particular time,
issuing an automated prompt to the end user informing of said elevated stress measure and the specific related task being performed.

10. The method according to claim 9, wherein when said elevated stress measure is a relative high task-specific stress score, relative to said baseline stress measure,
presenting the end user with said intervention options.

11. The method according to claim 10, wherein said intervention options include a request for a formal consultation, use of computerized decision support, request for additional data, or request to release said task and defer to another party.

12. The method according to claim 11, wherein when said elevated stress scores are associated with predetermined unacceptable outcomes, restrictions are placed on task complexity for the user, or mandatory stress interventions or remedial education/training is instituted for the user.

13. The method according to claim 12, wherein at one of completion of work, log-off of the computer system, or closing of said task,
providing the user with selected text from said database for said targeted speech for re-evaluation of stress; and
correlating said re-evaluated stress scores with recent stress levels measured in task performance using continuous speech, to determine user stress, fatigue, and uncertainty.

14. The method according to claim 8, wherein said speech analysis along with at least one of an experience level; job description, sensitivity or classification; past performance; safety record; emotional or physical state; or disciplinary action of the user; factor into an allowable stress level of the user for said task being performed.

15. The method according to claim 14, wherein administrative personnel are notified by electronic means of any identification or authentication failure.

16. The method according to claim 15, wherein the user is provided with an appeal process or can attempt an identification and authentication process after a designated time period.

17. The method according to claim 7, further comprising:
issuing an automated prompt by electronic means, to alert the an end user when said stress scores exceeds said predetermined threshold; and
providing an end user with intervention options.

18. The method according to claim 5, wherein said work restrictions or data access restrictions are invoked despite said deviation being below said baseline stress modulator stress score.

19. The method according to claim 5, wherein when said stress score exceeds said predetermined threshold, at least one of additional stress tests are triggered, technology selection and modification are initiated, security and compliance personnel are alerted, or electronic and/or physical surveillance of the user are initiated, with adjustment to said user-specific stress historical profile requirements for continuing performance, future technology or data access.

20. The method according to claim 19, wherein analysis of said stress scores, said user-specific historical stress profile, tasks being performed by the user, technology used, and said performance outcomes are analyzed by said processor, derive a user and context-specific stress inflection point, below which performance metrics deteriorate below an acceptable level.

21. The method according to claim 3, further comprising:
grouping users into similar peer groups used for creation of best practices guidelines and creation of adaptive technologies.

22. The method according to claim 1, further comprising:
completing a biometrics examination using a biometrics system, to identify and authenticate said user;
wherein said speech analysis and said biometrics examination are compared for identification and authentication of said user;
wherein at least one of said biometrics examination or said speech analysis device evaluate an emotional, physical, or cognitive state of the user in real-time prior to granting access to a computer system or other technology or equipment.

23. The method according to claim 22, wherein evaluation by said speech analysis device detects at least one of restfulness, sobriety, and emotion in said targeted speech.

24. The method according to claim 1, wherein any data on identification and authentication, or speech analysis, is recorded in said database for longitudinal analysis, quality assurance, or compliance.

25. The method according to claim 1, wherein said speech analysis to determine uncertainty includes at least one of ascertaining use of vague, ambiguous, or filler language, or repetitive patterns of language content associated with uncertainty and adverse outcomes for a specific task; and
wherein said speech analysis to determine uncertainty includes detection of deception; and
utilizing visual analysis, including eye tracking, to identify uncertainty.

26. The method according to claim 25, wherein when uncertainty speech is detected, an uncertainty prompt allows cross-reference of said uncertainty speech with said user-specific historical stress profile and performance outcomes indicators to identify a probability of adverse outcomes.

27. The method according to claim 26, further comprising:
providing automated prompts, alerts, or intervention options to an end user upon identification of uncertainty.

28. The method according to claim 27, wherein said intervention options include at least one of activation of computerized decision-support technologies, recommendation for consultation, deferral of a case of a patient to another colleague, identification of said case for subsequent quality assurance analysis and peer review, or automated search of an electronic medical record of said patient for additional clinical or imaging data.

29. The method according to claim 28, wherein said speech analysis is correlated with task complexity measures and context-specific clinical outcomes data to predict clinical significance of elevated stress levels correlated with user uncertainty and lack of diagnostic confidence.

30. The method according to claim 28, wherein said quality assurance and administrative oversight includes provision of individual, departmental, or community wide statistical analyses; and
wherein trending analyses, technology performance, tasks performed, collective and individual stress measures, and comparative analyses relative to large population-based statistics, are provided.

31. The method according to claim 30, further comprising:
generating an automated alert in an event that an end user did not adhere to departmental or institutional policies regarding response to stress response or interventions, or an adverse outcome of relatively severe magnitude was documented, or a higher than expected frequency of said stress outliers was recorded in said database.

32. The method according to claim 1, further comprising:
performing said speech analysis on the user when the user discontinues working, to document a specific level of stress at a time of work termination;
wherein said speech analysis is performed by said targeted speech of said user; and
wherein said targeted speech upon work termination is correlated with stress measurements of the user stored in said database.

33. The method according to claim 1, further comprising:
providing quantitative measures of statistical probability with each form of data output that provides the user with a mathematical probability that said data output is accurate and reproducible.

34. The method according to claim 1, further comprising:
providing a preliminary user-specific profile to said user based on said questionnaire which can be edited by the user before being provided to a peer reference group with shared characteristics, for educational purposes.

35. The method according to claim 34, further comprising:
linking adverse performance measures to specific speech analysis patterns, through prospective uncertainty measures.

36. The method according to claim 1, further comprising:
providing education and training to said user at pre-defined time intervals, upon user identification and authentication, or in an event of a critical action;
wherein when education and training has been invoked, an end user is provided with historical stress review, stress outliers, uncertainty, stress interventions, and best practices; and
wherein data analyses are provided in a user-preferred format, and in comparison with comparable data from similar end users.

37. A non-transitory computer-readable medium containing executable code for measuring speech for stress, fatigue and uncertainty, comprising:
providing a speech analysis device into which a user is directed by a computer system, to speak random text retrieved from a database and shown on a computer display;
obtaining user-specific identification related to user speech, which is used in conjunction with identification of said user, to provide identification and authentication data of said user;
providing a questionnaire to said user, to obtain data to establish a user-specific profile, and storing the provided data in said database;
providing targeted speech to said user on a computer display, as a series of randomly selected text strings retrieved from said database, for the user to speak into said speech analysis device for speech analysis identification and authentication, and after validating of said user, storing said targeted speech data in said database for analysis; and
obtaining intermittent stress measurements from said user during a task, through real-time speech analysis using targeted speech;
wherein after completion of said speech analysis for identification and authentication of said user, said speech analysis identifies fluctuations in stress measures caused by stress, fatigue, and uncertainty of said user; and
calculating a stress score for said user based upon said speech analysis.

38. A computer system for measuring speech for stress, fatigue and uncertainty, comprising:
at least one memory which contains at least one program which comprises the steps of:
providing a speech analysis device into which a user is directed by a computer system, to speak random text retrieved from a database and shown on a computer display;
obtaining user-specific identification related to user speech, which is used in conjunction with identification of said user, to provide identification and authentication data of said user;
providing a questionnaire to said user, to obtain data to establish a user-specific profile, and storing the provided data in said database;
providing targeted speech to said user on a computer display, as a series of randomly selected text strings retrieved from said database, for the user to speak into said speech analysis device for speech analysis identification and authentication, and after validating of said user, storing said targeted speech data in said database for analysis; and
obtaining intermittent stress measurements from said user during a task, through real-time speech analysis using targeted speech;
wherein after completion of said speech analysis for identification and authentication of said user, said speech analysis identifies fluctuations in stress measures caused by stress, fatigue, and uncertainty of said user; and
calculating a stress score for said user based upon said speech analysis at least one processor for executing the program.

* * * * *